United States Patent
Moncomble et al.

(10) Patent No.: US 10,942,563 B2
(45) Date of Patent: Mar. 9, 2021

(54) PREDICTION OF THE ATTENTION OF AN AUDIENCE DURING A PRESENTATION

(71) Applicant: Orange, Paris (FR)

(72) Inventors: Ghislain Moncomble, Plestin les Greves (FR); Patrick Rondet, Lannion (FR)

(73) Assignee: ORANGE, Paris (FR)

(*) Notice: Subject to any disclaimer, the term of this patent is extended or adjusted under 35 U.S.C. 154(b) by 0 days.

(21) Appl. No.: 16/329,429

(22) PCT Filed: Aug. 31, 2017

(86) PCT No.: PCT/FR2017/052314
§ 371 (c)(1),
(2) Date: Feb. 28, 2019

(87) PCT Pub. No.: WO2018/042133
PCT Pub. Date: Mar. 8, 2018

(65) Prior Publication Data
US 2019/0212811 A1    Jul. 11, 2019

(30) Foreign Application Priority Data

Sep. 1, 2016   (FR) ..................... 1658105

(51) Int. Cl.
*G06F 3/01*    (2006.01)
*A61B 5/11*    (2006.01)
(Continued)

(52) U.S. Cl.
CPC ............ *G06F 3/011* (2013.01); *A61B 5/1128* (2013.01); *A61B 5/168* (2013.01); *A61B 5/4803* (2013.01);
(Continued)

(58) Field of Classification Search
CPC ...... G06F 3/011; G06F 3/017; G06F 16/2455; G06F 16/2457; G06F 16/24575;
(Continued)

(56) References Cited

U.S. PATENT DOCUMENTS 10,708,659 B2 * 7/2020 Meredith ............. H04N 21/252
2008/0320082 A1 * 12/2008 Kuhlke ............... H04L 12/1822
709/205

(Continued)

OTHER PUBLICATIONS

Fan et al., "Yawning Detection for Monitoring Driver Fatigue", Proceedings of the Sixth International Conference on Machine Learning and Cybernetics, Hong Kong, Aug. 19-22, 2007.
(Continued)

*Primary Examiner* — Mahelet Shiberou
(74) *Attorney, Agent, or Firm* — David D. Brush; Westman, Champlin & Koehler, P.A.

(57) ABSTRACT

A method for predicting attention of an audience during a presentation by a speaker. The method includes: measuring vocal or gestural characteristics of the speaker of the presentation in progress and/or of characteristics of content of the presentation in progress; measuring a parameter of duration or of occurrence of the measured characteristics; consulting a database having a correspondence between vocal or gestural speaker characteristics and/or presentation content characteristics, parameters of duration or of occurrence which relate to these characteristics and information relating to the evolution of the attention level for these characteristics and these parameters and recovering the information relating to the evolution of the attention level corresponding to the measurements performed; and presenting to the speaker, a prediction of attention level on the basis of the information recovered relating to the evolution of the attention level. Also provided are a prediction device, learning phase and a learning device.

12 Claims, 4 Drawing Sheets

(51) Int. Cl.
| | |
|---|---|
| G09B 19/04 | (2006.01) |
| A61B 5/16 | (2006.01) |
| A61B 5/00 | (2006.01) |
| G10L 25/63 | (2013.01) |
| G09B 5/06 | (2006.01) |
| G06K 9/00 | (2006.01) |
| G06N 20/00 | (2019.01) |
| G10L 25/48 | (2013.01) |
| G16H 50/30 | (2018.01) |

(52) U.S. Cl.
CPC ......... *G06F 3/017* (2013.01); *G06K 9/00771* (2013.01); *G06N 20/00* (2019.01); *G09B 5/062* (2013.01); *G09B 19/04* (2013.01); *G10L 25/48* (2013.01); *G10L 25/63* (2013.01); *A61B 2503/12* (2013.01); *G06F 2203/011* (2013.01); *G06K 9/00302* (2013.01); *G16H 50/30* (2018.01)

(58) Field of Classification Search
CPC ..... A61B 5/1128; A61B 5/168; A61B 5/4803; G06N 20/00; G09B 5/062; G09B 19/04; H04N 21/4667; H04N 21/252; H04N 21/42203; H04N 21/4223; H04H 60/03; H04H 60/66; G10L 25/48; G10L 25/63
See application file for complete search history.

(56) References Cited

U.S. PATENT DOCUMENTS

| | | | |
|---|---|---|---|
| 2009/0138332 A1* | 5/2009 | Kanevsky | G11B 27/34 705/7.29 |
| 2011/0263946 A1 | 10/2011 | el Kaliouby et al. | |
| 2011/0295392 A1* | 12/2011 | Cunnington | H04N 7/15 700/90 |
| 2014/0363000 A1* | 12/2014 | Bowden | H04N 21/44222 381/56 |
| 2015/0332166 A1* | 11/2015 | Ferens | G06N 20/00 706/11 |
| 2016/0049094 A1 | 2/2016 | Gupta et al. | |
| 2016/0078369 A1* | 3/2016 | Frank | G06F 3/013 706/12 |
| 2017/0295404 A1* | 10/2017 | Meredith | H04H 60/33 |

OTHER PUBLICATIONS

Qing et al., "A Perclos-based Driver Fatigue Recognition Application for Smart Vehicle Space", Third International Symposium on Information Processing.

International Search Report dated Dec. 6, 2017 for corresponding International Application No. PCT/FR2017/052314, filed Aug. 31, 2017.

Written Opinion of the International Searching Authority dated Dec. 6, 2017 for corresponding International Application No. PCT/FR2017/052314, filed Aug. 31, 2017.

English Translation of the Written Opinion of the International Searching Authority dated Dec. 14, 2017 for rresponding International Application No. PCT/FR2017/052314, filed Aug. 31, 2017.

\* cited by examiner

US 10,942,563 B2

PREDICTION OF THE ATTENTION OF AN AUDIENCE DURING A PRESENTATION

CROSS-REFERENCE TO RELATED APPLICATIONS

This Application is a Section 371 National Stage Application of International Application No. PCT/FR2017/052314, filed Aug. 31, 2017, the content of which is incorporated herein by reference in its entirety, and published as WO 2018/042133 on Mar. 8, 2018, not in English.

FIELD OF THE DISCLOSURE

The present invention relates to the field of systems and methods for predicting the attention of an audience, and more particularly during a presentation by at least one speaker after a learning phase on a set of presentations that have already been given.

BACKGROUND OF THE DISCLOSURE

There are many ways to measure a person's attention in real time in various situations, for example behind the steering wheel of a car, when listening to a conference, or indeed when viewing an item of video content.

These methods are based, for example, on detections of body movement, eye movement, change of breathing rate, chatter, etc. This list is not exhaustive.

The aim of these measurements is to detect a decrease in the person's attention in order to intervene, either so as to stimulate the person or so as to change the viewed item of content or the context in which the person is situated.

In the case of presentations given by a speaker or several speakers, for example in the case of e-learning training courses, broadcast online, it is observed that it may be difficult to keep the attention of the learner, who is behind his screen and who does not have a group atmosphere or the context of the training course. The trainer may also not be aware of a decrease in attention when recording his presentation, in particular if this presentation is not provided live.

In the field of radio, it is also observed that homogeneous speech without a change of rhythm or speakers causes the listeners' attention to be lost, resulting in a loss of audience for the radio station. It is for this reason, whether in the field of radio or the audiovisual field, that stimuli or changes of rhythm are often provided, commercials are inserted, and reformulations are performed by other speakers in order to retain attention and listening over longer periods of time.

However, these tricks are implemented mostly empirically without knowing whether this has a real impact on attention and without knowing whether it is necessary to implement them.

Similarly, other more effective measures could be taken so as to keep the attention of the audience.

There is therefore a need to predict the attention of an audience in order to adapt an ongoing presentation so as to make it more attractive to an audience that is present or not yet present, without taking real-time attention measurements.

SUMMARY

The present invention aims to improve the situation.

To this end, it proposes a method for predicting the attention level of at least one audience during a presentation by at least one speaker. The method is such that it includes the following steps:

measuring vocal or gestural characteristics of the at least one speaker giving the ongoing presentation and/or measuring characteristics of content of the ongoing presentation;

measuring at least one parameter of duration or of occurrence of the measured characteristics;

consulting a database containing a correspondence between vocal or gestural characteristics of the speaker and/or characteristics of presentation content, duration or occurrence parameters linked to these characteristics and information in relation to the change in the attention level for these characteristics and these parameters, and recovering information in relation to the change in the attention level corresponding to the performed measurements;

presenting, to the at least one speaker giving the presentation, an attention level prediction on the basis of the recovered information in relation to the change in the attention level.

Thus, the speaker giving the presentation has an item of prediction information regarding the attention that the audience is paying or will pay to the presentation that he is currently giving. To this end, it is not necessary with this method to perform real-time measurements of the attention of the audience. Likewise, if a presentation is recorded so as to be broadcast later on, the method makes it possible to be informed with regard to an estimation of the change in the attention level that an audience may have, so as to adapt the rest of the presentation as needed.

The various particular embodiments mentioned hereinafter may be added independently or in combination with one another to the steps of the prediction method defined above.

In one particular embodiment, the information in relation to the change in the attention level comprises a probability regarding the change in the attention level, and this probability is presented to the at least one speaker.

The probability thus presented allows the speaker to know to what extent he should rely on the prediction of the change in the attention level that he has received. He is thus able to adapt his future actions as well as possible.

In one embodiment, the information in relation to the change in the attention level is corrected on the basis of an item of audience context information.

Specifically, depending on whether the audience contains one or more people, depending on the location in which the presentation is given or broadcast, depending on the time of day of the presentation, the temperature of the location in which an audience is situated, depending on the type of people present in the audience, depending on whether or not the members of this audience have eaten a substantial meal, etc., the attention of the audience may vary. The item of context information therefore makes it possible to improve or to modify the estimation of the attention level that has been measured.

In one particular embodiment, the information in relation to the change in the attention level is corrected on the basis of emotion measurements associated with the measured characteristics.

Specifically, the attention of the audience may change significantly depending on the content of the presentation, and more particularly key words or phrases, or, as a variant, particular images liable to generate emotion, the effect of which is to refocus the attention of the audience. The key words and/or key phrases, or the images that generate emotion, are determined by analyzing the audio and/or video signals of the presentation, for example by means of voice recognition and/or image recognition, and the database contains information that makes it possible to link these key words with an emotion measurement. Thus, depending on these key elements, the attention of the audience may also differ depending on whether or not the characteristic elements are linked to an additional emotion measurement.

The item of information in relation to the content of the presentation coupled with an associated emotion measurement therefore makes it possible to improve or to modify the estimation of the attention level that has been measured. This emotion measurement may also be different depending on the type of audience that is present or the context of the audience. The two items of emotion and context information may then be taken into account in order to improve or modify the estimation of the attention level.

In one embodiment, the method furthermore includes a step of determining recommendations for actions to be performed by the speaker so as to change the attention level of the at least one audience on the basis of the recovered information in relation to the change in the attention level and a step of presenting the determined recommendations to the at least one speaker.

Thus, the speaker knows how to adapt his presentation so as to increase the attention level of his present or future audience. He is able to optimize the ongoing presentation as well as possible.

In a phase prior to the prediction method, a learning phase is implemented. The invention thus relates to a method for learning information on the change in the attention level of at least one presentation audience. The learning phase is such that it includes the following steps:
  collecting attention level measurements from at least one audience for a set of presentations, a presentation being given by at least one speaker;
  indexing the presentations of the set by the collected attention level measurements;
  indexing the presentations of the set by measurements of vocal or gestural characteristics of the speakers and/or measurements of characteristics of content of the presentations;
  synchronizing the respective indexations so as to determine associations between characteristics and attention level measurements for the presentations of the set;
  determining the change in the attention levels by analyzing the associations determined for a set of characteristics or groups of characteristics and in accordance with at least one parameter of duration or of occurrence of these characteristics;
  recording, in a database, correspondences between the vocal or gestural characteristics of the speaker and/or the characteristics of presentation content, the duration or occurrence parameters linked to these characteristics and information in relation to the change in the attention level for these characteristics and these parameters.

This learning method may be implemented on a plurality of presentations given by the same speaker or by different speakers, so as to have a panel representative of the possible characteristics of presentations and speakers. The resulting database may be enriched as time goes on with measurements performed for new presentations; it may therefore evolve.

This learning method therefore makes it possible to associate information regarding the change in the attention level with characteristics linked to the ongoing presentation. The resulting database may be saved in the terminal implementing the prediction method, for example the presenter's terminal, so that said presenter has the attention level change information in a simple manner and without it being necessary to have measurement devices or even network access.

In one particular embodiment, the item of information in relation to the attention level comprises a probability of change calculated from the analysis of a repeatability rate of the changes determined on the set of presentations.

This therefore provides a measure of confidence regarding the attention level change information that is determined and presented to the speaker in the prediction method.

In order to improve the correspondences between characteristics and attention level change information recorded in the database, the information in relation to the change in the attention level recorded in the database is corrected on the basis of an associated item of audience context information or on the basis of emotion measurements associated with the corresponding characteristic elements.

Thus, the learning method also takes into account the characteristics of the contexts of the audiences, which will make it possible, when using said database, to select audience contexts corresponding to those expected for a presentation to which the method will be applied. The same context characteristics may also be taken into account if emotion measurements are also applied, these measurements also being able to differ from one context to another.

Correlatively, the invention targets a device for predicting the attention of at least one audience of a presentation given by at least one speaker. The device is such that it includes:
  a measurement and detection module for detecting vocal or gestural characteristics of the at least one speaker giving the ongoing presentation and/or characteristics of content of the ongoing presentation and for measuring at least one parameter of duration or of occurrence of the detected characteristics;
  a module for consulting a database in order to determine information in relation to the change in the attention level, the database containing a correspondence between vocal or gestural characteristics of the speaker and/or characteristics of presentation content, duration or occurrence parameters linked to these characteristics and information in relation to the change in the attention level for these characteristics and these parameters;
  a user interface for presenting, to the at least one speaker giving the presentation, an attention level prediction on the basis of the recovered information in relation to the change in the attention level.

The invention relates to a terminal that includes a prediction device such as described.

This terminal and this device have the same advantages as the method described above. According to another aspect, the invention targets a prediction system such that it includes a prediction device described above and a learning device including:
  a module for collecting attention level measurements from an audience taken on a set of presentations, a presentation being given by at least one speaker;
  an indexing module for indexing presentations of the set by measurements of the attention level of an audience, on the one hand, and indexing presentations of the set by measurements of vocal or gestural characteristics of the speakers and/or measurements of characteristics of content of the presentations, on the other hand;
  a synchronization module for synchronizing the respective indexations so as to determine associations between characteristics and attention level measurements for the presentations of the set;
  an analysis module for determining changes in the attention levels by analyzing the associations determined for a set of characteristics or groups of characteristics and in accordance with a parameter of duration or of occurrence of these characteristics;

a module for recording, in a database for recording correspondences between the vocal or gestural characteristics of the speaker and/or the characteristics of presentation content, the duration or time parameters linked to these characteristics and information in relation to the change in the attention level for these characteristics and these parameters.

This learning device may advantageously be inserted into a server of a communication network. It may also be inserted into a terminal.

This device has the same advantages as the learning method described above that it implements.

The invention finally targets a prediction system such that it includes a learning device such as described and a prediction device such as described.

The invention also targets a computer program including code instructions for implementing the steps of the prediction method such as described and/or of the learning method such as described above when these instructions are executed by a processor.

It also targets a computer-readable information medium on which there is recorded such a computer program comprising instructions for executing the steps of the prediction method and/or of the learning method such as described.

BRIEF DESCRIPTION OF THE DRAWINGS

Other features and advantages of the invention will become more clearly apparent on reading the following description, given purely by way of nonlimiting example and with reference to the appended drawings, in which.

DETAILED DESCRIPTION OF ILLUSTRATIVE EMBODIMENTS

Figure 1A:
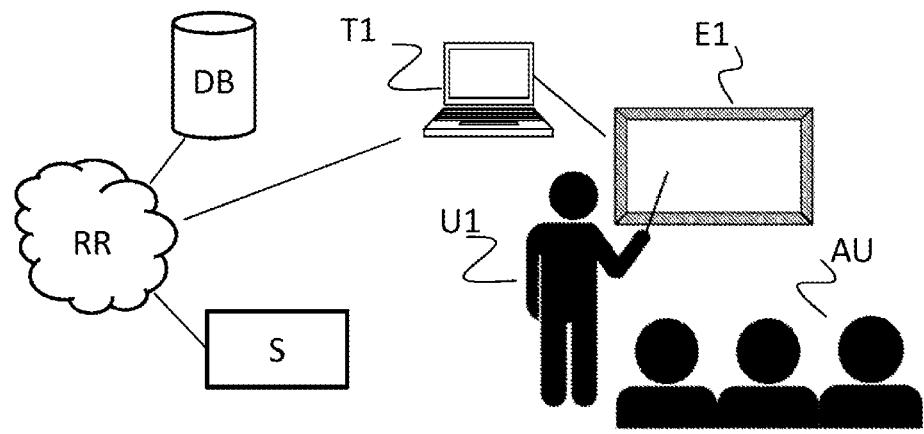
FIGS. 1a and 1b illustrate examples of a system for predicting the attention of an audience in real-time or recorded presentation or conference contexts, conducted by a speaker, face-to-face in a room with an audience, or online through a network communication.

FIG. 1a shows an exemplary system and context in which the prediction method according to the invention is able to be implemented. A speaker U1 is currently giving a presentation in front of an audience AU. He performs his presentation using a screen E1 and a terminal, here a computer T1. The computer T1 is for example linked to an Internet network R and is thus able to be connected to a server S on which a learning method has been implemented so as to form a database DB2.

The learning method may also be implemented in the terminal T1 in another exemplary embodiment. It will be described in more detail with reference to FIG. 2a.

The terminal T1 or the server S implements a prediction method according to the invention. This will be described later with reference to FIG. 2b.

To implement the prediction and/or learning method in the terminal T1, said terminal is associated with at least one microphone, not shown, capable of capturing the oral presentation of the speaker. The sound thus captured will then be analyzed so as to determine audio characteristics of the speaker. In one exemplary embodiment, the terminal T1 is also associated with a camera, not shown, that is filming and detecting the movements of the speaker. These movements may also be analyzed so as to determine other characteristics of the speaker during the ongoing presentation.

Figure 1B:
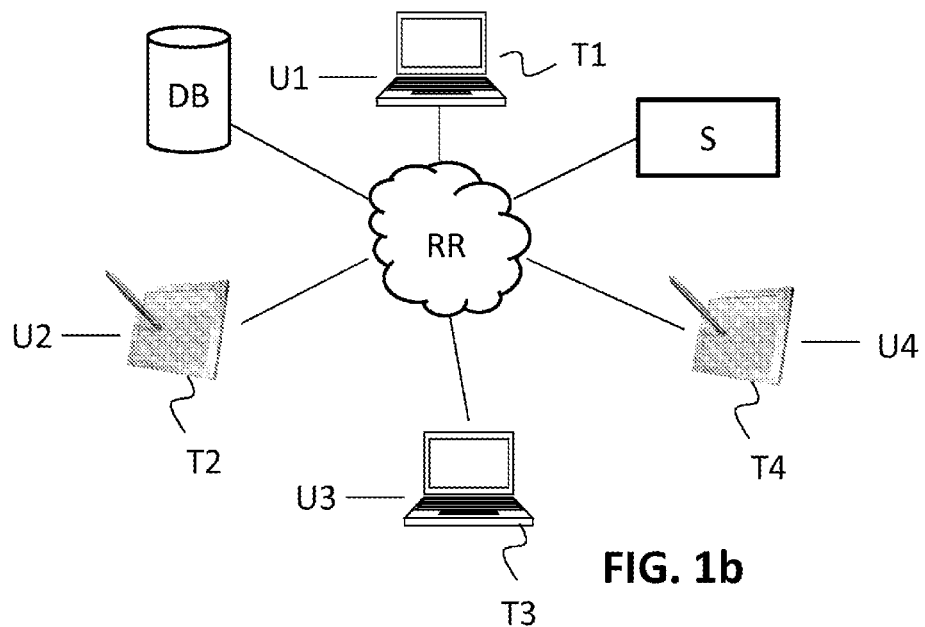

FIG. 1b describes another context of a prediction system according to the invention. In this context, the speaker U1 giving a presentation or online training course of MOOC (for "Massive Open Online Course" in English) type is in front of his computer or terminal T1 and broadcasting his presentation through the network R to a set of users U2, U3 and U4, each user being in front of their respective terminal T2, T3 and T4. These users thus represent the audience of the ongoing presentation. In the same way as for FIG. 1a, a server S may, in one embodiment, implement the learning method and/or the prediction method according to the invention. In another embodiment, the prediction method is implemented in the terminal T1 and the learning method in the server S, or else both the prediction method and the learning method are implemented in the terminal T1.

In the same way as for FIG. 1a, the terminal T1 is associated for example with a microphone and with a camera so as to detect both the audio characteristics of the speaker and the movement characteristics.

The database DB2 is fed following the learning phase and contains correspondences between characteristic elements of the speaker, such as vocal or gestural characteristics of the speaker, and/or of the presentation, such as characteristics of content of the presentation, duration or occurrence parameters linked to these characteristics or elements, and information in relation to the change in the attention level for these characteristics and these parameters.

These prediction systems are described here as examples, but other presentation systems may be possible. For example, an MOOC-type presentation may be recorded by the presenter of this MOOC so as to be broadcast later on online or so as to be recorded on the network so as to be available at any time. In this case, the audience consists of a single person who consults the presentation alone and when he wishes.

Figure 2A:
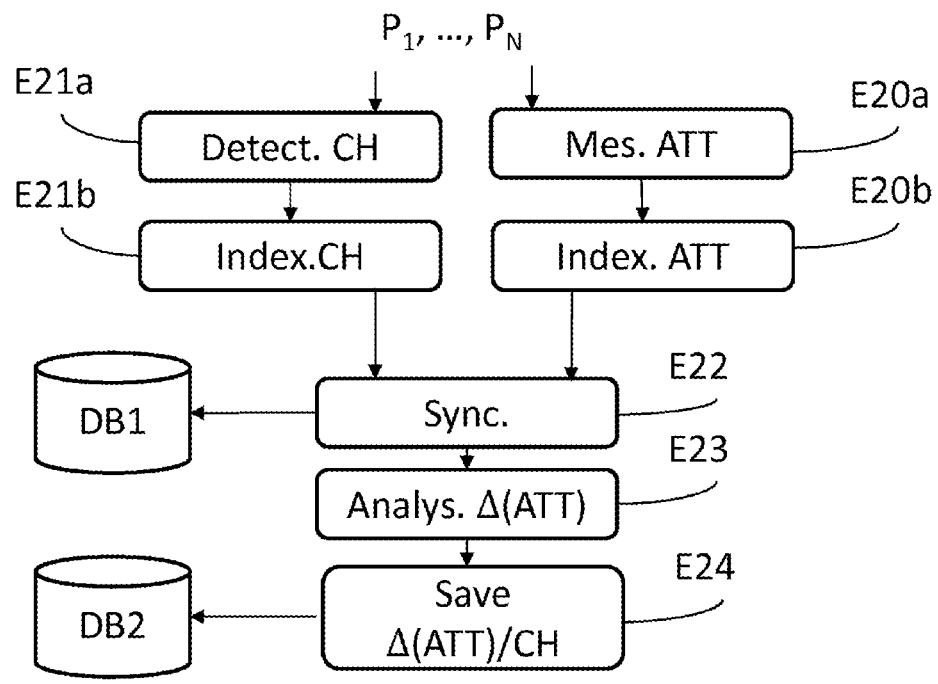
FIG. 2a illustrates, in the form of a flowchart, the main steps of a method for learning information on change in the attention level, prior to the prediction phase, in one embodiment of the invention.

With reference to FIG. 2a, a description is now given of the steps implemented during the learning method in one embodiment of the invention. This learning method constitutes a learning phase implemented prior to the steps of the prediction method.

For this learning method, a set of presentations that have already been recorded is available for example on the network or in a database either of the network or of the piece of equipment implementing this learning phase. Thus, a server of the network or else a terminal of a user, for example of the speaker giving the presentation, may implement this phase.

On the basis of this presentation set $P_1$ to $P_N$, a step E21a of detecting characteristics from the speaker giving the presentation and/or of the content of the presentation is implemented.

For this purpose, analysis is performed on each of the presentations $P_i$ of the set of presentations $P_1$ to $P_N$, which will be referred to as reference set or set of reference presentations. Analysis is performed on characteristics of the presenter, the speaker giving the presentation. For example, an audio measurement sensor measures the speaker's sound level, the prosody characteristics over time, that is to say the phenomena of accentuation and intonation (variation in pitch, duration and intensity) of the speaker's voice, over the course of the presentation. Another sensor of video type is able to measure the gestures made by the speaker during his recorded presentation and the pauses that he may take. Other analysis elements make it possible to measure for example possible noise during the presentation. The analysis that is performed also makes it possible to determine the characteristics specific to the content itself, for example the way in which the presentation was filmed, the change in the framing, the presence of key words, of key images or sequences of images, for example using an image analysis algorithm. All of these analysis elements are listed and indexed, in step E21b, on the time line of the progression of the reference presentation. On the basis of this same reference set, a step E20a is implemented so as to measure the attention of an audience.

To this end, the learning device measuring this attention level is for example equipped with a camera capable of detecting facial movements, the blinking of the eyes, the frequency of yawning, etc.

Several techniques for measuring the attention level may be used for this step E20a. The techniques described hereinafter are not exhaustive. The method implemented here may use only one of these techniques or else several of them; the combination of several techniques then affords additional accuracy for the attention measurement that is ultimately obtained.

The attention level measurements thus obtained are then indexed, in step E20b, on the time line of the progression of the reference presentation.

One attention level measurement technique is for example a technique based on the analysis of the faces in the audience. For example, when the audience is made up of people consulting their computer in order to follow a conference or online training course, capturing the image of the viewer's face makes it possible to see when said viewer turns away from his screen, if he moves away, moves or is replaced with another face. In all of these cases, this means that the user's attention has decreased.

Another possible measurement is based on measuring the frequency of blinking of the eyes of the people in the audience. When the number of blinks exceeds a certain threshold or when the user's eyelids are closed for too long, this means that the user is starting to become drowsy, and is therefore losing attention.

These techniques are well known in the field of driver alertness measurements. They may be used here to measure a participant's attention to the presentation. One example of such a technique is described in the document entitled "A PERCLOS-based Driver Fatigue Recognition Application for Smart Vehicle Space" by the authors Wu Qing, Sun BingXi, Xie Bin and Zhao Junjie, in "Third International Symposium on Information Processing" (ISIP), pages 437-441 in 2010.

Another measurement technique is based on the frequency of yawning of the people in the audience. Yawning is a typical reaction induced by fatigue. This is manifested in a prolonged and uncontrolled opening of the mouth that is very different from other deformations of the lips and that is able to be measured using image analysis techniques. The opening of the mouth during a yawn is wider than the opening of the mouth during speech. Such a technique is described for example in the article entitled "Yawning detection for monitoring driver fatigue" by the authors Xiao Fan, Bao-Cai Yin, Yan-Feng Sun, in "Proceedings of the Sixth International Conference on Machine Learning and Cybernetics" in Hong Kong, 19-22 Aug. 2007.

A detection of a change in orientation of a listener's head may also indicate a decrease in attention. Specifically, a forward dropping of the head is indicative of the person's fatigue. If this detection is further correlated with other detections, described above, then this indicates this person's loss of attention.

In even more technologies, the level of ambient chatter noise may also be detected and may thus indicate that the audience is not attentive to the presentation being given to them.

These various attention level measurement techniques may be applied to several people forming the audience. In this case, the determined attention levels, as well as the change in these attention levels during the analyzed presentation, are kept in association with the audience in question. For one and the same presentation and at a given moment, several attention levels may thus be determined for different groups of people in the audience.

For a more precise approach to measuring the attention level, an individual measurement may be preferred over an overall approach. In this case, the attention measurement is performed for each of the people in the audience, the overall attention level then being determined by adding up the unit attention levels.

In one particular embodiment, an item of audience context information is associated with the attention level measurement. Specifically, depending on the context of the audience, the attention measurement may vary.

For example, depending on the time of day of the presentation, a user's attention level may be different for one and the same presentation. Specifically, it is known that a state of drowsiness may be boosted at the beginning of digestion within one hour following a meal, while alertness reaches its maximum two to three hours after a meal. If the attention level of one and the same presentation is measured at different times and for similar people, it is possible to determine the correction to be made to the measured attention level on the basis of the time.

Likewise, other context parameters may require a correction of the attention level. For example, a date, a duration of sunshine, the heat in a room or the number of people attending the presentation may be context information to be provided so as to correct the measured attention level.

The type of people present in the audience may also cause the attention level to vary, for example if the people are old, young, from a different culture, speaking a different language, etc.

Once these attention measurements have been determined and, where appropriate, associated with a correction parameter, they are indexed on the time line of the reference presentation currently being analyzed.

In one variant embodiment, it is also possible to measure an emotion level of the audience depending on the content of the presentation. In this case, an emotion level measurement is indexed in addition to the other indexations described above.

This type of measurement is for example carried out using known facial analysis techniques that detect for example a smile, a particular grimace, crying, etc.

These emotion levels are linked to attention levels. Specifically, a smile for example may characterize renewed attention toward the presented content.

This emotion indexation of the reference presentations is collated with indexations of characteristics of the content of the presentations, for example with the existence of key words, of key images or sequences of images.

In step E22, the various indexations performed in steps E20b and E21b are collated. For this purpose, the two types of indexation are synchronized so that the audience attention measurement, indexed at a moment in time of the presentation, is associated with the characteristic or characteristics of the speaker and/or of the presentation for this same moment in time of the presentation.

Thus, at E22, following this synchronization, an association is obtained between attention level measurement elements and elements of characteristics of the presentation and of the speaker. This association may be recorded in a database DB1. For the variant including emotion measurements, an association is made between characteristic elements of the content, the measured emotions and the measured attention level.

In the simplified case where the durations of the time lines of the presentations broadcast at various times and indexed according to various characteristics are identical, the synchronization will be limited to making the beginnings of said time lines coincide.

If these durations are different, for example when interrupting a presentation for questions and answers, the resynchronizations may be periodic on the basis of sequences detected as being common (for example by analyzing the soundtrack and comparison).

In step E23, the various synchronizations performed for each presentation between characteristics of the speaker, characteristics of the presentation and the attention level measurements are used by an analysis module to determine the change in the attention level. This module determines probabilities of correlation between a decrease or an increase observed with regard to the attention measurement and various groups of characteristic elements of the presentation and/or of the speaker. In this step, a cause-effect duration parameter between groups of characteristic elements of the speaker and/or of the presentation and the changes in attention measurements are also determined, in order to distinguish for example the groups of elements that generate an attention loss rate or an attention increase rate either immediately or after a period of repetition of these elements.

The influence of a parameter of occurrence of appearance of a group of characteristic elements in a presentation is also determined in this step.

The list is not exhaustive, and other determinations would be possible, such as for example the interactions between groups of characteristic elements.

Thus, step E23 makes it possible to determine a change in the attention level on the basis of a group of characteristic elements of the speaker or else of the content of the presentation, or even of both thereof, and on the basis of at least one parameter of duration or of occurrence of these characteristic elements.

For example, a monotonous tone of a speaker giving a presentation for a duration of several minutes gradually lowers the attention level, whereas the speaking of key words or the projection of key images (for example of violence or a scenic landscape) may drastically increase the attention level.

In one advantageous embodiment, attention increase and decrease thresholds are defined so as to retain only significant characteristics of the speaker and/or of the presentation. The threshold may for example be 1 or 2%.

As these correlation analyses are performed on the set of reference presentations, step E23 also implements verification of the repeatability of the changes determined for each of the reference presentations. If a correspondence between characteristic elements or groups of characteristic elements and attention level decrease or attention level increase rate is found in several presentations of the set, then this correspondence is recorded in a database DB2, also called learning base.

A calculation of the probability of change in the attention level may be performed on the basis of this analysis of the repeatability rate of the changes in attention level that are determined on the reference set. This probability may then be recorded in the database DB2, in association with the change/characteristics correspondence that corresponds thereto.

Thus, in step E24, there is recorded in a database DB2 a set of information in relation to the change in the attention level (increase or decrease in the level, rate of change, i.e. a progressiveness index of the change, for example abrupt or gradual, a probability of the change, for example the repeatability rate in the reference set, etc.) in correspondence with elements or groups of characteristic elements of the speaker and/or of the presentation and at least one parameter of duration or of occurrence of these elements.

Said base DB2 may, in its simplified version, be limited to separate backup files, or to retention of information in a relational database table separate from other tables forming DB1. One advantage of said separation of the base DB2 is of course that it is subsequently able to be used separately from the base DB1 within the context of the prediction process described with reference to FIG. 2b. Therefore, rather than having to use the very large base DB1 with the various presentation indexations, only the results of the analyses contained in the base DB2, namely the list of the groups of characteristic elements and the associated duration or occurrence parameters that bring about a probability of change in attention and the associated change information (as described above), are necessary. The small potential size of the base DB2 therefore allows autonomous use in embedded mode, without the need for a network connection to a server dedicated to the database DB1.

In one variant embodiment, several reference sets may be provided. The various sets are for example created on the basis of the topics of the presentations or else on the basis of the type of audience.

Thus, classifying the reference presentations into several groups makes it possible to find more common points between the presentations and thus more repeatability of the determined changes.

An exemplary record in the database DB2 may be, for a silence characteristic of the speaker with a duration parameter of a few seconds, a correspondence with an item of information in relation to the change in the attention level, which is an immediate increase in attention.

Another example is a correspondence between a sound level of the speaker's voice that remains unchanged for several minutes and a gradual decrease in the attention level.

The change of speaker may for example be associated with an immediate increase in the attention level, and in the same way the change of framing of the display of the presentation may be associated with an immediate increase in attention.

A rate of increase or decrease of the attention level, that is to say a progressiveness index of the change, may also be associated with the triggering characteristic elements.

Thus, at the end of this learning phase, the database DB2 is enriched by a set of information in relation to the change in the attention level in correspondence with characteristic elements or groups of elements of the presentation and/or of speakers and parameters of duration or of occurrence of these elements.

It is also possible to include therein the average time and its variance between a triggering event, that is to say a characteristic element, and its effect in terms of the change in the attention level.

The information on the change in attention level is characterized by a tendency to increase or decrease, as the case may be, a rate of change, that is to say an index linked to the progressiveness of the change in attention, so as to distinguish between immediate effects and effects smoothed over a longer period and a probability of this tendency being applicable. An item of information in relation to the average time of occurrence of the change in attention may also be recorded.

Figure 2B:
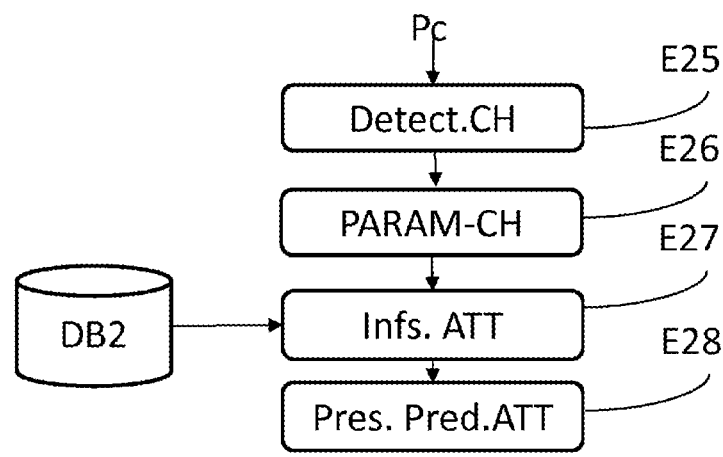
FIG. 2b illustrates, in the form of a flowchart, the main steps of a prediction method according to one embodiment of the invention.

FIG. 2b illustrates the steps implemented during the prediction method according to the invention. This method is implemented for example in the terminal T1 of the presenter or else in a server S of the communication network R. It is applicable to an ongoing presentation, conducted by at least one speaker. Reference will be made to current presentation Pc.

A first step E25 performs analysis of this presentation. This analysis concerns, for example, the characteristics of the speaker, his voice, his sound level, his gestures, his pause or breathing times, etc.

In order to measure the characteristics of the voice of the speaker or speakers, a voice analysis module is provided in the prediction device, performing voice analysis on the sound captured by a microphone associated with the presentation equipment.

The analysis may also concern the content of the presentation, what is presented on the screen, the frequency of page changing, the framing of what is shown, the colors used, the detection of key words, of key images, etc.

This type of analysis may be performed for example by detecting an action of the presenter for the page change, by an image analyzer for detecting colors or movements or key images of said images, etc.

In E26, there is associated, with this detection of characteristic elements of the presentation and/or of the speaker, determination of at least one parameter of duration of these characteristic elements or of repetition over time of these characteristic elements.

A search is performed in the database DB2 of these characteristic elements of the speaker and/or of the presentation and of the associated parameters in E27 so as to find therein the corresponding information in relation to the change in the probable attention level.

This information therefore makes it possible to obtain a prediction of the attention level that the presentation will receive if the corresponding characteristic elements persist for the associated duration or are repeated in accordance with the associated instance and if the speaker does not change his presentation or his characteristics.

This item of attention level prediction information is presented to the speaker giving the presentation in E28 so that he is able to react on his presentation in real time.

A probability of this attention level prediction and of the rate of change may also be presented.

In one particular embodiment, the prediction of the attention level is associated with determination of recommendations for actions to be performed on the presentation so as to change the attention level in the desired direction, followed by the presentation of these recommendations to the speaker.

One exemplary recommendation is to ask to increase the sound level of the speaker's voice if it has been detected that the voice level decreases over time and that the time for which the attention level decreases is exceeded.

To this end, the recommendations may be determined by:
  an interface for selecting the desired direction of change in the attention level: decrease attention (if for example the presenter absolutely has to mention a subject but he prefers that no one remember it) or increase it. A default mode that simplifies the interface from the point of view of the speaker would be that of improving attention with respect to a given relevant level, which is fixed for example with reference to the beginning of the presentation, a phase in which attention is conventionally considered to be at its maximum.
  a means for determining the characteristics for changing the attention level of the audience or audiences with an acceptable probability. This determination may be performed using the following steps:
    a) selecting a first set of groups of characteristics in the base DB2 that influence attention in the desired direction,
    b) filtering the set on the basis of the number of occurrences of each of these groups of characteristics that have already been implemented (determined) during previous phases of the ongoing presentation, and, on the basis of the time since the last occurrence encountered for each group of characteristics (if the last occurrence was a long time ago, it may logically be considered that it no longer has an impact on the effectiveness of the group of characteristics in question)
    c) and lastly selecting, from the subset resulting from the filtering, the group of characteristics whose probability of impact is highest. As a variant, in case of equality, various possibilities would be presented, and/or one would be chosen randomly from among the remaining subset.

For example, the recommendation could consist in proposing to broadcast an image, for example of a scenic landscape, whose impact on the probability of change in attention is known. This suggestion could also consist in proposing groups of key words to be spoken.

The presenter is thus able to modify his presentation on the basis of the recommendations and thus improve the attention level of his audience.

The presenter is thus informed of potential changes in attention of his audience, even if there is no ongoing measurement of the attention of the audience or even if there is no audience. Specifically, the presentation may be simply being recorded without anyone present for subsequent broadcast to an audience. As a variant, the presenter may simply be rehearsing the presentation that he will give later, in order to be more effective at the appropriate time.

Thus, it is not necessary to have attention-measuring equipment to be informed of the change in attention level in real time.

In one particular embodiment, this information regarding the change in the attention level may be corrected on the basis of context information linked to the present or intended audience. This information may be for example the time of day of the presentation or the one intended to be broadcast, the number of people in the audience, the temperature of the room in which the presentation is given, etc.

The correction to be made is for example recorded in the databases DB1 and DB2 in association with the characteristics of the speaker and/or of the presentation.

In another variant linked to the emotion measurement that was able to be performed in the learning phase, a weighting of the attention level may be provided and recorded in the database DB2. This weighting is then applied to the information in relation to the change in the attention level obtained during the prediction method when the triggering characteristic elements are associated with emotion measurements, as described above.

This weighting is thus able to correct the change prediction presented to the speaker.

The attention level prediction may be presented in various forms. In one exemplary embodiment, it may be presented to the speaker by way of a differently colored symbol. For example, the color intensity may correspond to the rate of change of the attention level. This presentation may be given on the presenter's personal screen or, if light is involved, on the microphone thereof. The change in the attention level may also be represented by an arrow pointing upward in the event of an increase and downward in the event of a decrease, of a greater or lesser height depending on the associated rate of change. Another way to display the result of this prediction is for example to display an average value of the attention level at the beginning of the sequence, and then, as the presentation progresses, to represent the attention level predictions by way of a curve that may run below or above this average value. The prediction regarding the level change is then readily legible to the presenter. As a variant, a % representing the accuracy rate established on the basis of learning data for the ongoing prediction may be presented. The time within which the attention change prediction is expected may also be presented in seconds, for example.

Thus, such a prediction method may allow the presenter of a training course or of a presentation to improve it by taking into account the changes in attention level that are presented to him. He may for example train prior to a real presentation in order to optimize his contribution and avoid the decreases in attention level. He may also give different presentations based on different audience context information. For example, depending on the time of day of the broadcasting of the presentation, he may make the presentation more dynamic with changes of speaker or of tone if the presentation is broadcast at a time of digestion, and provide it in a less dynamic manner if not.

As another variant, if the presentations are broadcast to the audience at a later point (for example an MOOC might not be broadcast live, but may be given at a time T and then broadcast in 3 sessions later on at times T1, T2 and T3), the prediction method and the suggestion method could lead to the broadcasting of 3 different variants of the same MOOC video, one of which is both shorter and more dynamic because the session is planned at the beginning of the afternoon over an area and period for which a high temperature is expected.

Figure 3:
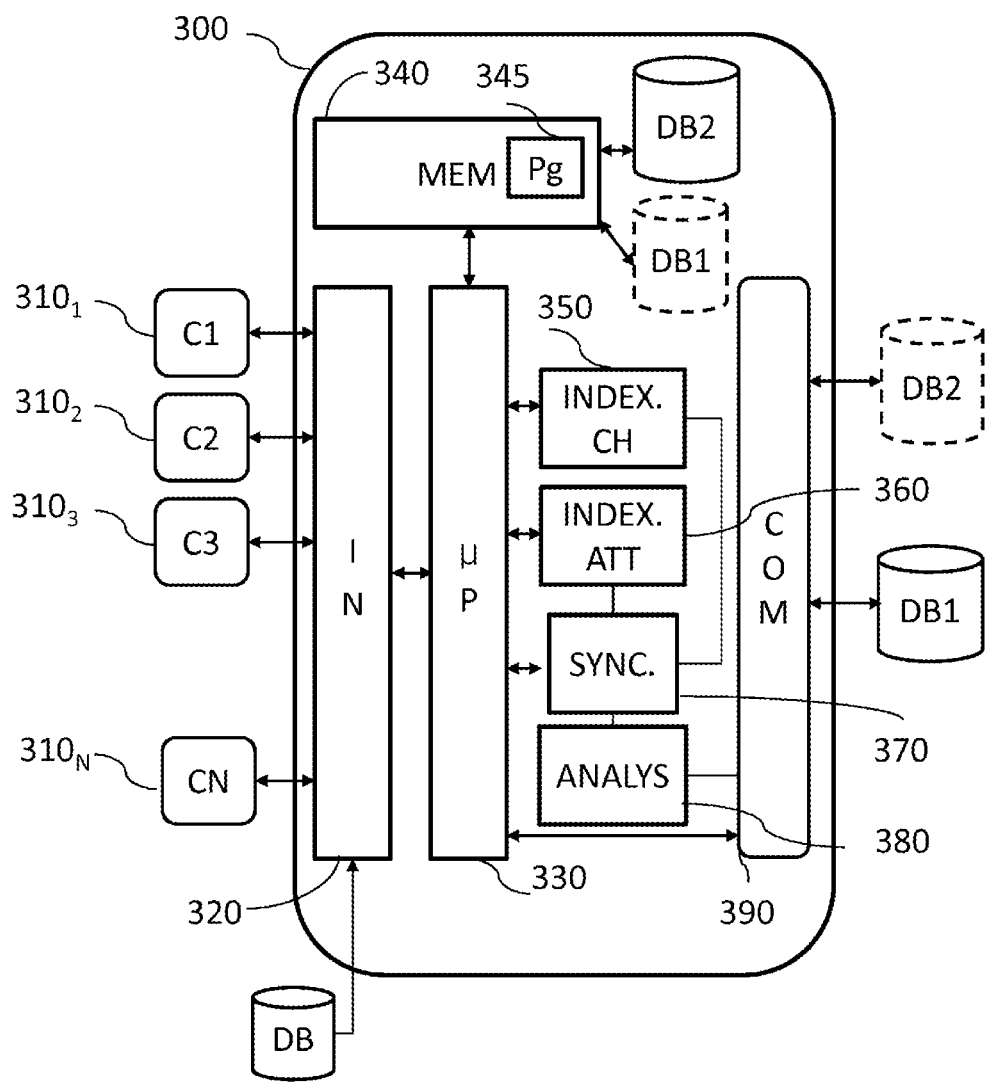
FIG. 3 illustrates a hardware configuration of a learning device able to implement the learning method according to one embodiment of the invention.

FIG. 3 shows a simplified hardware architecture of one embodiment of a learning device implementing the learning method described with reference to FIG. 2a.

It will be noted that the invention that is described here may be implemented by way of software and/or hardware components. In this context, the terms "module" and "entity" used in this document may correspond either to a software component or to a hardware component, or else to a set of hardware and/or software components, capable of implementing the function or functions described for the module or entity in question. This device is equipped with a measurement collection interface 320 capable of collecting the measurements captured by the sensors C1 to CN shown here at $310_1$, $310_2$, $310_3$ and $310_N$.

These sensors are intended to measure the vocal characteristics of the speaker or speakers, for example by virtue of one or more microphones, to measure the movement characteristics of the speaker, for example by virtue of a camera, on the one hand, and to measure the attention level of the audience, on the other hand. To this end, a camera may also be provided.

The device comprises a processing unit 330 equipped with a processor and driven by a computer program Pg 345 stored in a memory 340 and implementing the learning phase according to the invention.

On initialization, the code instructions of the computer program Pg are for example loaded into a RAM memory, not shown, and executed by the processor of the processing unit 330. The processor of the processing unit 330 implements the steps of the learning method described above with reference to FIG. 2a, according to the instructions of the computer program Pg.

In the exemplary embodiment of the invention under consideration, the device 300 therefore comprises an input interface for receiving presentations that have already been recorded from a database DB containing one or more sets of reference presentations.

It comprises a module for indexing characteristics specific to the speaker giving the presentation and/or characteristics specific to the content of the presentation. To this end, the indexing module receives measurements collected by the interface 320 and performed by the sensors C1 to CN so as to determine the loudness level of the presenter, his tone, his silences or else the ambient loudness level. It also receives information regarding the changes in the content presented, for example a change in the framing, a change of presentation page, a zoom on the image, a key word, a key image, from the interface 320.

The learning device also includes a module for indexing attention level measurements. These attention level measurements are obtained by the interface 320 that collects the measurements performed by the sensors C1 to CN and in particular the data measured by one or more cameras, on the basis of which algorithms for detecting blinking of the eyes or yawning or else positioning of the head are implemented so as to obtain an attention level measurement.

This attention level measurement is indexed on the presentation currently being processed of the set of reference presentations. A synchronization module 370 is also provided so as to synchronize the two types of indexation and to obtain an association between the characteristic elements of the speaker and/or of the presentation from the module 350 and the attention level measurements from the indexing module 360.

This association of elements may be recorded in a database DB1 integrated into the device or available through a communication network via a communication module 390.

An analysis module 380, driven by the processor 330, analyzes the associations of measured attention levels and characteristics for the reference presentations, and determines a change in the attention level according to at least a parameter of duration or a parameter of occurrence of the characteristics.

The analysis makes it possible to associate a characteristic or a succession of characteristics with a change in attention level. It also makes it possible to determine a duration or number of occurrences for which the measured characteristic changes the attention level.

At the output of the analysis module 380, a correspondence is made between characteristic elements or groups of characteristic elements of the speaker and/or of the presentation, duration or occurrence parameters associated with these elements with information in relation to the change in the attention level of the audience.

Since these correspondences are performed for the presentation set or sets in the database DB, in one particular embodiment, the analysis module determines the repeatability rate of the defined associations. Only the correspondences that have a sufficient repeatability rate may be stored in the database DB2. This database may be stored on a remote server accessible through a communication network via the communication module 390 of the device. The communication network is an IP network, for example.

In another embodiment, this database DB2 is integrated into the learning device. It may also be sent or downloaded to a terminal, for example that of a presentation speaker.

This learning device is either a network server communicating with the presenter's terminal or the presenter's terminal itself.

Figure 4:
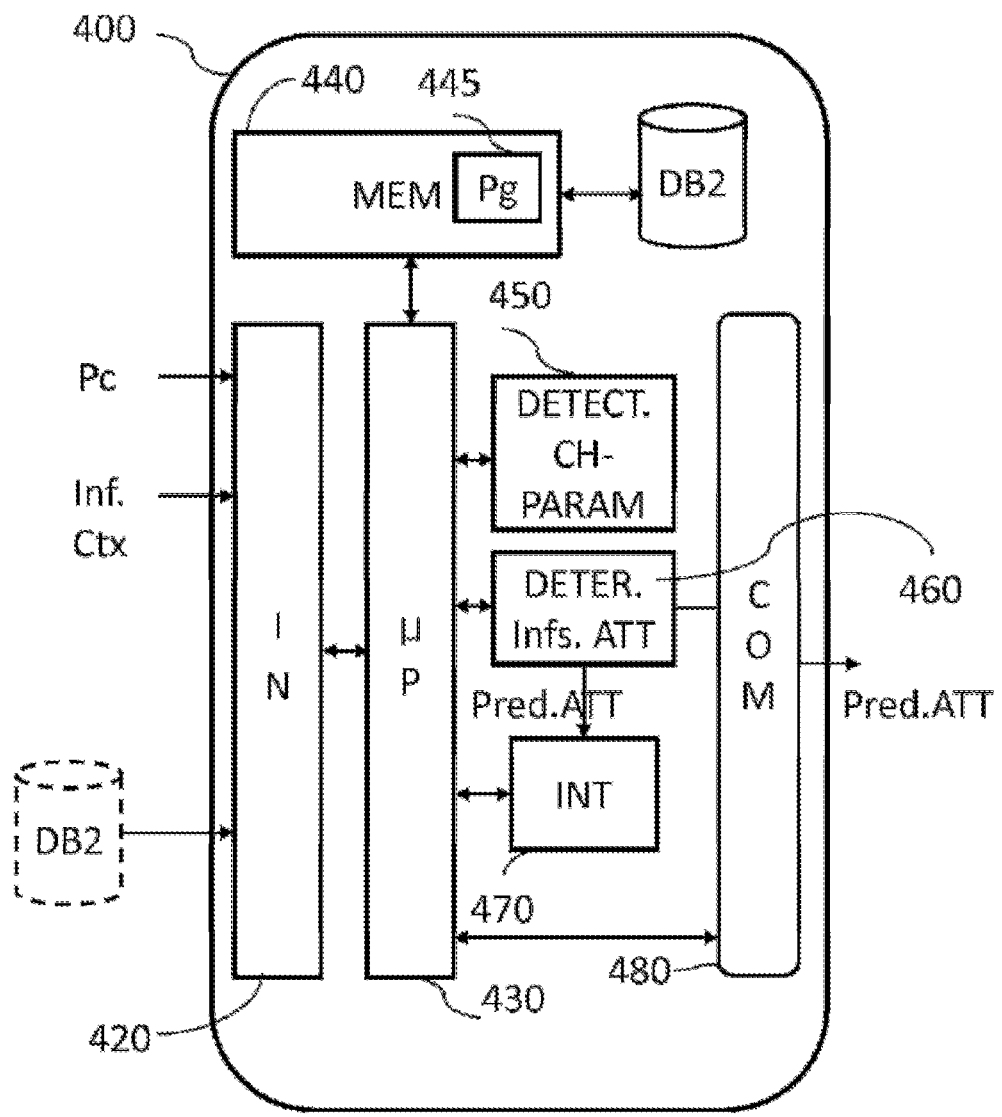
FIG. 4 illustrates a hardware configuration of a prediction device according to one embodiment of the invention.

FIG. 4 shows a simplified hardware architecture of one embodiment of a prediction device 400 implementing the prediction method described with reference to FIG. 2b.

It will be noted that the invention that is described here may be implemented by way of software and/or hardware components. In this context, the terms "module" and "entity" used in this document may correspond either to a software component or to a hardware component, or else to a set of hardware and/or software components, capable of implementing the function or functions described for the module or entity in question. This device is equipped with an input interface capable of consulting a database DB2 internal to the device or available on a communication network and containing correspondences between characteristic elements of the speaker and/or of presentations, duration or occurrence parameters linked to these elements and information in relation to the change in the audience attention level for these elements and parameters, and as learned during a learning phase such as described with reference to FIG. 2a.

The device comprises a processing unit 430 equipped with a processor and driven by a computer program Pg 445 stored in a memory 440 and implementing the prediction method according to the invention.

On initialization, the code instructions of the computer program Pg are for example loaded into a RAM memory, not shown, and executed by the processor of the processing unit 430. The processor of the processing unit 430 implements the steps of the prediction method described above, according to the instructions of the computer program Pg.

In the exemplary embodiment of the invention under consideration, the device 400 therefore comprises an input interface for receiving the data stream of the ongoing presentation Pc. This interface may also receive context information on the audience of this presentation (Inf.Ctx).

It comprises a detection module 450 for detecting characteristics of the speaker or speakers giving the presentation and/or the ongoing presentation. A parameter of duration of the detected characteristic or of repetition (of occurrence) of this characteristic is also detected by the module 450. Thus, characteristic elements are obtained at the output of this detection module. The processor 430 implements the module for determining information in relation to the change in the attention level by looking up, in the database DB2, via the interface 420 or via the memory 440, whether a correspondence containing the detected element and the associated parameter is recorded. Where applicable, a prediction regarding the change in the attention level resulting from the information thus determined in relation to the change in the attention level is sent to the user interface 470 so that this change prediction is presented to the speaker giving the ongoing presentation. Recommendations for actions to be performed by the speaker may also be sent to this user interface, in order for said user to change the attention level of his presentation.

This prediction device may be contained within the terminal of the speaker giving the presentation. In this case, the prediction is displayed directly on the screen of his terminal via the user interface or else on an accessory connected to his terminal, such as a microphone for example.

The device may also be integrated into a server of a communication network, for example an IP network; in this case, the prediction is presented to the speaker giving the presentation via a communication module 490 that transmits the item of information to the presenter's terminal.

The item of audience context information may be used by the determination module 460 so as to correct the determined change where applicable.

In one embodiment of the invention, both the learning device and the prediction device are contained in one and the same piece of equipment, either the speaker's terminal or a network server. In another embodiment, these two devices are remote, the learning method and the prediction method being implemented in a system comprising the two devices communicating with each other via a network.

Although the present disclosure has been described with reference to one or more examples, workers skilled in the art will recognize that changes may be made in form and detail without departing from the scope of the disclosure and/or the appended claims.

The invention claimed is:

1. A method for learning information on a change in the attention level of at least one presentation, wherein, the method comprises the following acts performed by a the learning device:
   collecting attention level measurements from at least one audience for a set of presentations, a presentation being given by at least one speaker;
   indexing the presentations of the set by the collected attention level measurements;
   indexing the presentations of the set by measurements of vocal or gestural characteristics of the speakers and/or measurements of characteristics of content of the presentations;
   synchronizing the respective indexations so as to determine associations between characteristics and attention level measurements for the presentations of the set;
   determining the change in the attention levels by analyzing associations determined for a set of characteristics or groups of characteristics and in accordance with at least one parameter of duration or of occurrence of these characteristics;
   recording, in a database, correspondences between the vocal or gestural characteristics of the speaker and/or the characteristics of presentation content, the duration or occurrence parameters linked to these characteristics and information in relation to the change in the attention level of audience for these characteristics and these parameters.

2. The method as claimed in claim 1, wherein the item of information in relation to the change in the attention level of audience comprises a probability of change calculated from the analysis of a repeatability rate of the changes determined on the set of presentations.

3. The method as claimed in claim 1, wherein the information in relation to the change in the attention level of audience recorded in the database is corrected on the basis of an associated item of audience context information or on the basis of emotion measurements associated with the corresponding characteristics.

4. The method of claim 1, further comprising constructing a database based on the set of presentations, wherein the database is used in a method for predicting attention level of the at least one audience during a presentation by the at least one speaker, wherein the method for predicting attention level comprises the following acts performed by a set of at least one device:

measuring with at least one sensor at least one of vocal or gestural characteristics of the at least one speaker giving the ongoing presentation or characteristics of content of the ongoing presentation;

measuring with the at least one sensor at least one parameter of duration or of occurrence of the measured characteristics;

consulting the database constructed via the learning phase based on the set of presentations and containing a correspondence between at least one of the vocal or gestural characteristics of the speaker or characteristics of presentation content, duration or occurrence parameters linked to these characteristics and information in relation to change in the attention level of audience for these characteristics and these parameters, and recovering information in relation to the change in the attention level of audience corresponding to the performed measurements; and presenting on a user interface, to the at least one speaker giving the presentation, an attention level prediction of the audience on the basis of the recovered information in relation to the change in the attention level of audience.

5. The method as claimed in claim 4, wherein the information in relation to the change in the attention level of audience comprises a probability regarding the change in the attention level, and wherein this probability is presented to the at least one speaker.

6. The method as claimed in claim 4, wherein the information in relation to the change in the attention level of audience is corrected on the basis of an item of audience context information.

7. The method as claimed in claim 4, wherein the information in relation to the change in the attention level of audience is corrected on the basis of emotion measurements associated with the measured characteristics.

8. The method as claimed in claim 4, furthermore comprising determining recommendations for actions to be performed by the speaker so as to change the attention level of the at least one audience on the basis of the recovered information in relation to the change in the attention level of audience and a step of presenting the determined recommendations to the at least one speaker.

9. A prediction system, comprising:
a prediction device for predicting attention of at least one audience of a presentation given by at least one speaker, wherein the prediction device comprises:
at least one processor;
at least one non-transitory computer-readable medium comprising instructions stored thereon, which when executed by the at least one processor configure the at least one processor to perform acts comprising:
detecting measurements of at least one of vocal or gestural characteristics of the at least one speaker giving the ongoing presentation or characteristics of content of the ongoing presentation and measuring at least one parameter of duration or of occurrence of the detected characteristics; and
consulting a database constructed via a learning phase based on a set of presentations in order to recover information in relation to the change in the attention level of audience corresponding to the detected measurements, the database containing a correspondence between at least one of vocal or gestural characteristics of the speaker or characteristics of presentation content, duration or occurrence parameters linked to these characteristics and information in relation to the change in the attention level of audience for these characteristics and these parameters; and
a user interface configured to present, to the at least one speaker giving the presentation, an attention level prediction of the audience on the basis of the recovered information in relation to the change in the attention level; and
a learning device including:
a module for collecting attention level measurements from an audience taken on a set of presentations, a presentation being given by the at least one speaker;
an indexing module for indexing presentations of the set by measurements of the attention level of an audience, on the one hand, and indexing presentations of the set by measurements of vocal or gestural characteristics of the speakers and/or by measurements of characteristics of content of the presentations, on the other hand;
a synchronization module for synchronizing the respective indexations so as to determine associations between characteristics and attention level measurements for the presentations of the set;
an analysis module for determining changes in the attention levels by analyzing the associations determined for a set of characteristics or groups of characteristics and in accordance with a parameter of duration or of occurrence of these characteristics;
a module for recording, in a database for recording correspondences between the vocal or gestural characteristics of the speaker and/or the characteristics of presentation content, the duration or time parameters linked to these characteristics and information in relation to the change in the attention level for these characteristics and these parameters.

10. The prediction system as claimed in claim 9, wherein the learning device is a server.

11. A non-transitory computer-readable information medium on which there is recorded a computer program comprising instructions for executing a prediction method for predicting attention of at least one audience of a presentation given by at least one speaker, when the instructions are executed by a processor, wherein the prediction method comprises:
detecting measurements of at least one of vocal or gestural characteristics of the at least one speaker giving the ongoing presentation or characteristics of content of the ongoing presentation and measuring at least one parameter of duration or of occurrence of the detected characteristics; and consulting a database constructed via a learning phase based on a set of presentations in order to recover information in relation to the change in the attention level of audience corresponding to the detected measurements, the database containing a correspondence between at least one of vocal or gestural characteristics of the speaker or characteristics of presentation content, duration or occurrence parameters linked to these characteristics and information in relation to the change in the attention level of audience for these characteristics and these parameters, the learning phase includes:

collecting attention level measurements from at least one audience for a set of presentations, a presentation being given by at least one sneaker;

indexing the presentations of the set by the collected attention level measurements;

indexing the presentations of the set by measurements of vocal or gestural characteristics of the speakers and/or measurements of characteristics of content of the presentations;

synchronizing the respective indexations so as to determine associations between characteristics and attention level measurements for the presentations of the set;

determining the change in the attention levels by analyzing associations determined for a set of characteristics or groups of characteristics and in accordance with at least one parameter of duration or of occurrence of these characteristics;

recording, in a database, correspondences between the vocal or gestural characteristics of the speaker and/or the characteristics of presentation content, the duration or occurrence parameters linked to these characteristics and information in relation to the change in the attention level of audience for these characteristics and these parameters; and a user interface configured to present, to the at least one speaker giving the presentation, an attention level prediction of the audience on the basis of the recovered information in relation to the change in the attention level of audience.

12. A terminal comprising the prediction device as claimed in claim 9.

* * * * *